(12) United States Patent
Faasse, Jr.

(10) Patent No.: US 7,094,944 B2
(45) Date of Patent: Aug. 22, 2006

(54) MEDICAL ADHESIVE DRESSING

(76) Inventor: Adrian L. Faasse, Jr., 17108 Ridgeback Rd., Carmel Valley, CA (US) 93924

( * ) Notice: Subject to any disclaimer, the term of this patent is extended or adjusted under 35 U.S.C. 154(b) by 171 days.

(21) Appl. No.: 10/071,713

(22) Filed: Feb. 7, 2002

(65) Prior Publication Data
US 2002/0107466 A1 Aug. 8, 2002

Related U.S. Application Data

(60) Provisional application No. 60/267,036, filed on Feb. 7, 2001.

(51) Int. Cl.
*A61F 13/00* (2006.01)
*A61F 15/00* (2006.01)

(52) U.S. Cl. .............. 602/57; 602/58; 602/54; 602/43; 602/42

(58) Field of Classification Search ........... 602/41–59; 206/440, 441; 128/888, 889
See application file for complete search history.

(56) References Cited

U.S. PATENT DOCUMENTS

| | | |
|---|---|---|
| 4,372,303 A | 2/1983 | Grossmann et al. |
| 4,485,809 A | 12/1984 | Dellas |
| 4,598,004 A | 7/1986 | Heinecke |
| 4,600,001 A | 7/1986 | Gilman |
| 4,614,183 A | 9/1986 | McCracken et al. |
| 4,753,232 A | 6/1988 | Ward |
| 4,875,473 A | 10/1989 | Alvarez |
| 4,884,563 A | 12/1989 | Sessions |
| 4,917,112 A | 4/1990 | Kalt |
| 4,917,929 A | 4/1990 | Heinecke |
| RE33,353 E | 9/1990 | Heinecke |
| 5,000,172 A | 3/1991 | Ward |
| RE33,727 E | 10/1991 | Sims |
| 5,088,483 A | 2/1992 | Heinecke |
| 5,160,315 A | 11/1992 | Heinecke et al. |
| 5,336,162 A | 8/1994 | Ota et al. |
| 5,520,629 A | 5/1996 | Heinecke et al. |
| 5,531,855 A | 7/1996 | Heinecke et al. |
| 5,599,289 A | 2/1997 | Castellana |
| 5,628,724 A * | 5/1997 | DeBusk et al. ............... 602/58 |
| 5,722,943 A | 3/1998 | Sessions |
| 5,738,642 A | 4/1998 | Heinecke et al. |
| 5,951,505 A | 9/1999 | Gilman et al. |
| 6,043,406 A * | 3/2000 | Sessions et al. ............. 602/41 |

* cited by examiner

*Primary Examiner*—Henry Bennett
*Assistant Examiner*—Amanda Wieker
(74) *Attorney, Agent, or Firm*—Price, Heneveld, Cooper, DeWitt & Litton, LLP

(57) ABSTRACT

Medical adhesive dressings are disclosed having handle members adhered to polymeric film layers by a layer of adhesive which adheres firmly to the polymeric film layer, but does not adhere to skin or to the silicone coated surface of a release liner. A portion of the handle extends beyond an edge of the polymeric film to facilitate separation of the film from the release liner, and handling thereof during application to a patient. The adhesive adhering the polymeric film to the patient's skin is more aggressive with respect to the patient's skin than the adhesive on the undersurface of the handle is to the polymeric film, whereby the handle can be peeled away from the polymeric film after the film has been applied to the patient.

34 Claims, 2 Drawing Sheets

MEDICAL ADHESIVE DRESSING

CROSS-REFERENCE TO RELATED APPLICATION

This application claims priority under 35 U.S.C. § 119(e) on U.S. Provisional Application No. 60/267,036 entitled IV HOLD-DOWN/WOUND DRESSING DEVICE, filed Feb. 7, 2001, by Adrian L. Faasse, Jr., the entire disclose of which is incorporated herein by reference.

BACKGROUND OF THE INVENTION

The present invention generally relates to medical adhesive dressings including wound dressings, intravenous hold-downs and drapes.

A typical medical adhesive dressing comprises a relatively thin film, such as a thin urethane film, adhered to some type of handling portion which is somewhat stiffer and thus facilitates handling the thin polyurethane film. The handling portion of the dressing must extend beyond, i.e. overhang an edge or edges of the film, so that the dressing can be handled by the applicator, without the applicator's fingers contacting the adhesive coated surface of the thin film. Since the handling portion is adhered to the upper surface of the thin film, the manufacturer must either apply adhesive only to those portions of the handling member which actually engage the top surface of the thin film, or alternatively the manufacturer must adhesively coat the entire undersurface of the handling portion, and put a separate release liner on the exposed adhesive coated undersurface portions which extend beyond the perimeter of the thin film. This is necessary so that the handling portion does not stick to the fingers of the applicator, or to the release liner. Adherence of the handling portion to the release liner would make it difficult to separate the release liner from the dressing.

In yet another variation, manufacturers use heat sealed bonds to bond a carrier material to a backing material. Heat sealed bonds are controlled by manipulating the temperature and the duration of the heating process.

Any of these variations creates substantial expense in manufacturing the medical adhesive dressings. Selective adhesive coating of the handling portion requires cutting handling portions from a web stock material, then aligning and selectively coating the handling portions with an adhesive. Other known variations require the cost of adding a release liner, or the additional step of nonpermanently heat sealing a carrier to the top face of the backing.

SUMMARY OF THE INVENTION

In the present invention, a polymeric film is coated on a first side with a first adhesive providing releasable adhesion to a release liner and firm adhesion to skin after the liner is removed. The release liner covers the adhesively coated first side of the polymeric film and the release liner extends beyond at least one edge of the polymeric film. At least one handle is bonded to a second non-adhesive side of the polymeric film with a pressure sensitive adhesive. The pressure sensitive adhesive has a firm but releasable affinity for the polymeric film, and a low affinity for skin and the release liner. The handle is placed on the second side of the polymeric film so that at least a portion of the handle extends beyond at least one edge of the polymeric film. The polymeric film can be removed from the release liner by grasping at least one extending portion of at least one handle and peeling the polymeric film away from the release liner. At least one handle can then be used to control the polymeric film as it is applied to a patient's skin. The first adhesive on the first side of the polymeric film adheres more aggressively with respect to a patient's skin than the pressure sensitive adhesive on the undersurface of the handle adheres to the polymeric film. The handle can be removed from the polymeric film once the polymeric film is adhered to a patient's skin.

These and other objects, advantages and features of the invention will be more fully understood and appreciated by reference to the written specification and appended drawings.

DESCRIPTION OF THE PREFERRED EMBODIMENT

Figure 1:
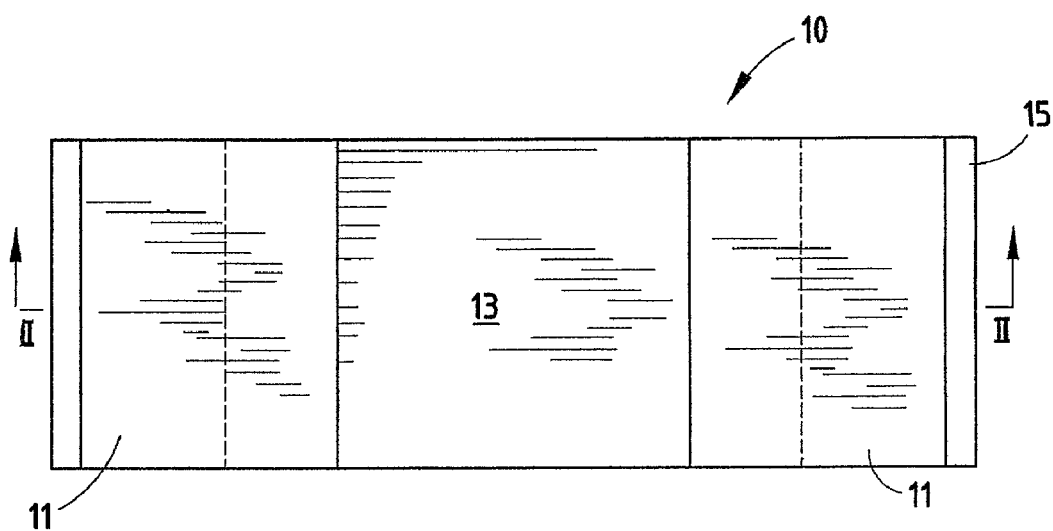
FIG. 1 is a plan view of a medical adhesive dressing made in accordance with the present invention.

The medical adhesive dressings of this invention may embody wound dressings, intravenous hold-downs and surgical drapes.

Medical adhesive dressing 10 of the first embodiment comprises a pair of handling members or handles 11 attached by a layer of adhesive 12 to a rectangularly shaped, thin layer of polymeric film, such as polyurethane film 13 (FIGS. 1 and 2), having an adhesive coated side or face and an opposite side or face that is not coated with an adhesive. The side or face of the film that is not coated with an adhesive is referred to as the non-adhesive side. A suitable thickness for film 13 is about 1 mil. Handles 11 extend beyond the ends of polymeric film 13, as indicated by the dashed lines in FIG. 1, and as can be seen from the cross section in FIG. 2. Polymeric film layer 13 is coated on its undersurface with a layer of adhesive 14, which releasably adheres to a silicone coating 16 on the top surface of release liner 15.

Figure 2:
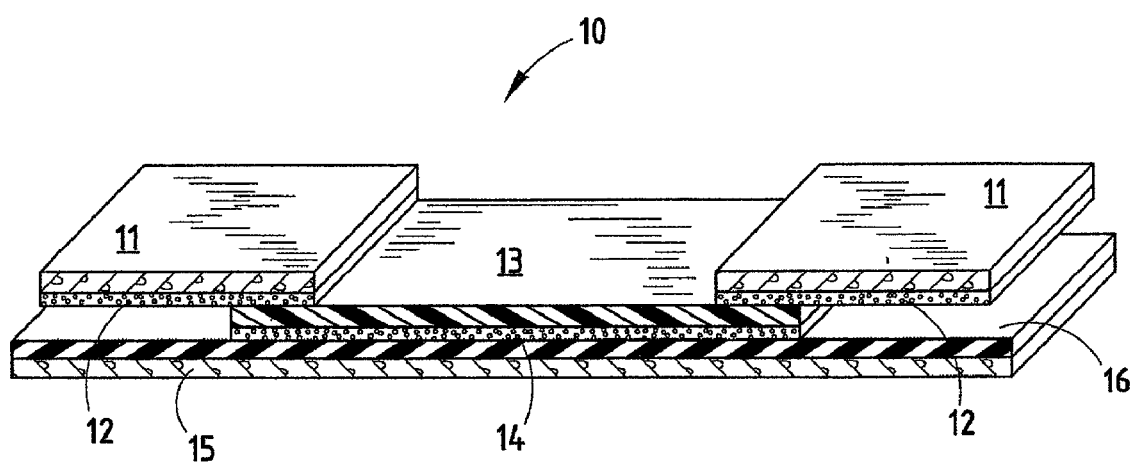
FIG. 2 is a cross-sectional view of the medical adhesive dressing of FIG. 1, taken along line II—II.

Handles 11 are preferably made of plastic or paper, or silicone coated paper, with the silicone coat on the upper surface thereof. Paper handles 11 are shown in FIGS. 1 and 2. The entire undersurface of each of handles 11 is coated with a pressure sensitive adhesive, which is moderately aggressive with respect to polymeric film 13, but which does not adhere or adheres less aggressively to either the silicone coating 16 on release liner 15 or to human skin. In this way, a user can readily fold back the end portion of release liner 15 to expose the end of one of the handles 11, and the exposed handle 11 can then be used to peel film 13 away from release liner 15. The adhesive of layers 12 is "moderately aggressive" in that handles 11 remain attached to polymeric film 13 when it is peeled away from release liner 15, and while it is being handled and applied to the patient's skin. However, pressure sensitive adhesive 12 is less aggressive with respect to its adhesion to polymeric film 13, than is the adhesion of layer 14 on the undersurface of film 13 toward human skin. As a result, handles 11 can be peeled away from polymeric film 13, once film 13 is applied to the patient.

One type of adhesive which we have found useful for layers 12 on the undersurface handles 11 is low tack removable acrylate-based adhesives with a peel adhesive level of approximately three ounces. Other useful adhesives include, but are not limited to, silicone, urethane, synthetic rubber and natural rubber. Adhesives of this type can be formulated to have essentially no or very little adhesion to the human skin or to the silicone coating 16 on the release liner 15, but still adhere firmly but releasably to film 13.

A type of adhesive found useful for layer 14 on the undersurface of polymeric film 13 is a permanent acrylate-based pressure sensitive adhesive designed for skin, with a peel adhesion level of approximately 50 ounces. Other useful adhesives include, but are not limited to, silicone, urethane, synthetic rubber and natural rubber. Such adhesives can be formulated to adhere releasably to the silicone coated surface 16 of the release liner 15. At the same time, they can be formulated to adhere firmly to the human skin, such that the polymeric film 13 will not peel away from the human skin unless someone intends to do so.

Figure 3:
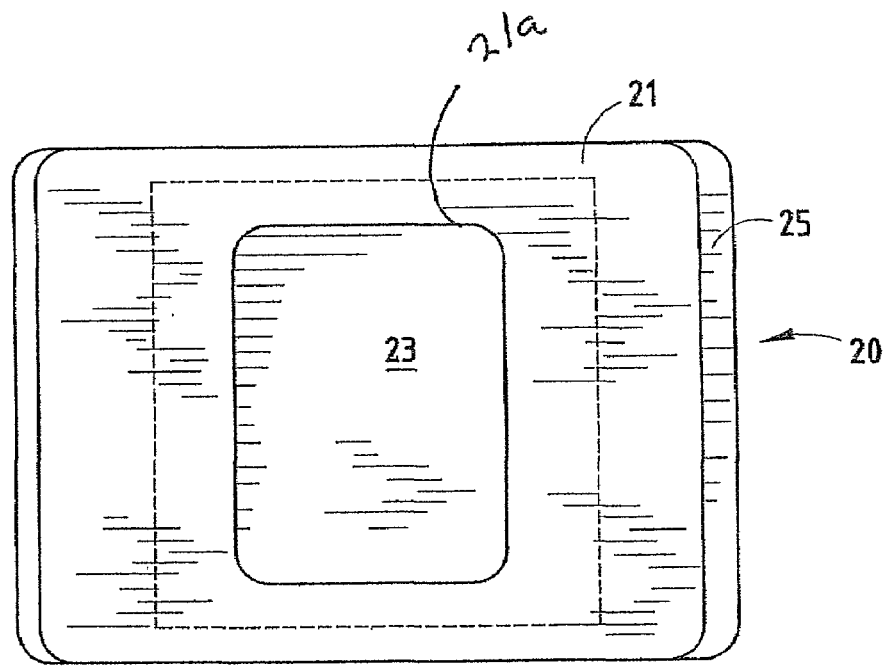
FIG. 3 is a plan view of an alternative embodiment of the medical adhesive dressing made in accordance with the present invention.

FIG. 3 discloses an alternative embodiment 20 of a medical adhesive dressing which is constructed in the same way as the FIGS. 1 and 2 embodiment, except that the handling portion 21 is rectangularly shaped, and includes a central opening 21a, which exposes polymeric film layer 23 thereunder. Adhesively coated polymeric film 23 is adhered to a release liner 25, in the same manner as polymeric film layer 13 is adhered to release liner 15. In use, one bends back release liner 25 to expose an edge of handling frame 21, and handling frame 21 is grasped and used to peel adhesively coated polymeric film 23 away from release liner 25. It is similarly used to handle film 23 until it is applied to a patient's skin, at which time handle frame 21 is peeled away from the top surface of polymeric film 23.

Figure 4:
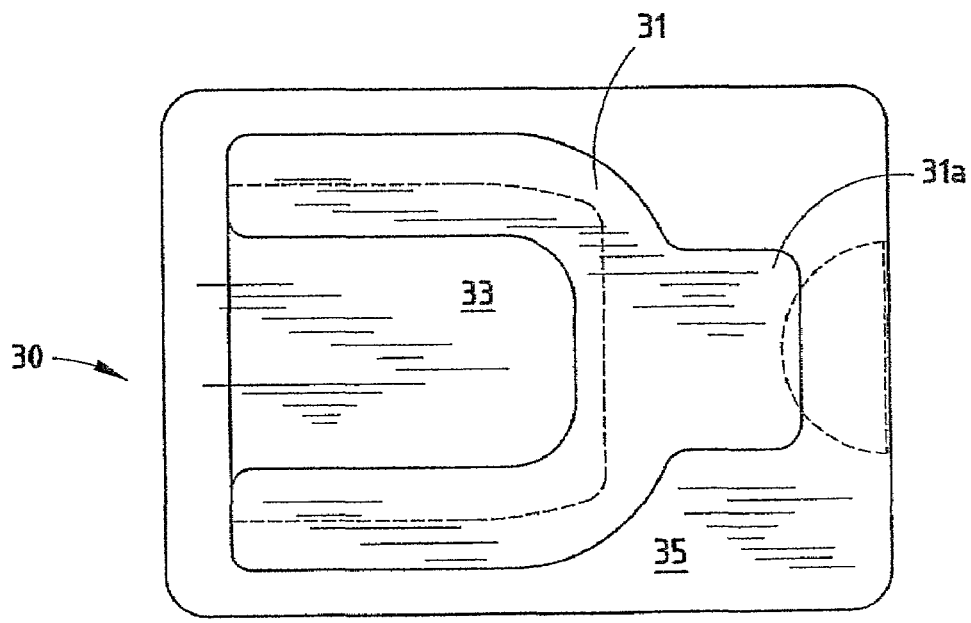
FIG. 4 is a plan view of a third alternative embodiment of the medical adhesive dressing made in accordance with the invention.

FIG. 4 discloses yet a third embodiment 30, in which the handle 31 is U-shaped, having an end tab 31a projecting from the base of the U-shape. Handle 31 is adhered by its pressure sensitive adhesive layer to the top surface of polymeric film 33 along three sides thereof, with the fourth side edge being exposed as shown in FIG. 4. More specifically, the handle 31 includes a pair of spaced legs secured along two edges of the polymeric film 33 and a base joining the space legs secured along and extending beyond a third edge of the polymeric film. This entire assembly is then applied to a silicone coated release liner 35, in the same manner as are the embodiments discussed above. In use, one folds back release liner 35 in the vicinity of tab 31a, grasps tab 31a and peels the assembly of handle 31 and polymeric film 33 away from release liner 35. The applicator then applies polymeric film 33 to the patient's skin, and then peels handle 31 away from the applied polymeric film 33.

It will be appreciated by those skilled in this art that there are a number of different ways in which the various embodiments of the invention can be manufactured. What is common to all, is that the present invention makes it possible to apply pressure sensitive adhesive to the entire undersurface of the handles (11, 21 or 31) of the products, and press the handles onto the non-adhesive side of the polymeric film (13, 23 or 33) with adhesive coated portions of the handles extending beyond (overhanging) the edges of the film, and press the release liner (15, 25 or 35) onto the adhesive side of the film, with the release liner extending beyond the edges of the film to the same extent as the handles, to a lesser extent, or further if desired.

This is a greatly simplified manufacturing process, as compared to adhesively coating only a portion of the undersurface of handles 11, or alternatively non-permanently heat sealing a carrier to the top surface of the backing, or alternatively applying a piece of release liner to the exposed, overhanging portions of handles 11.

In a continuous process, a web of polymeric film can be used which is narrower than the width of the corresponding release liner web and handle stock web. The handle stock web can be die cut to define spaced window openings for the FIG. 3 alternative embodiment, or could be applied as two spaced ribbons for the FIGS. 1 and 2 embodiments. The polymeric web can be pressed to the release liner web with a reinforcing casting sheet applied to the non-adhesive side of the web to give it handling stability. The casting sheet is then separated from the assembled film and liner webs prior to pressing the handle web to the non-adhesive side of the film.

Alternatively, the polymeric film web might be pressed first to the handle web (unitary with window opening or as spaced ribbons), with a temporary release liner web on the adhesive side of the film to give it handling stability. The temporary release liner web is then peeled away before the assembled handle and film webs are joined to the final product release liner. Once the webs are assembled, they can be die cut at spaced intervals to define the individual products.

The foregoing are preferred embodiments of the invention and changes and variations can be made without departing from the spirit and broader aspects of the invention, as defined in the appended claims, which are to be interpreted in accordance with the principles of patent law, including the Doctrine of Equivalents.

The invention claimed is:

1. A medical adhesive device comprising:
   a polymeric film;
   an adhesive coated surface comprising a first adhesive coated on a first side of said polymeric film;
   a release liner covering the adhesive coated surface of said polymeric film and extending beyond at least a first edge of said polymeric film;
   a handle adhered to a second non-adhesive side of the polymeric film with a pressure sensitive adhesive, with a portion of said handle projecting beyond said first edge of said polymeric film and overlying said release liner;
   said first adhesive on said first side of said polymeric film adhering more aggressively to skin than said pressure sensitive adhesive adheres to said polymeric film, whereby said handle can be removed from said polymeric film once said polymeric film is adhered to a patient's skin.

2. The medical adhesive device of claim 1, in which said polymeric film comprises a polyurethane film.

3. The medical adhesive device of claim 2, in which said release liner is a silicone coated release liner.

4. The medical adhesive device of claim 1, in which said handle is generally U-shaped, having a pair of spaced legs secured along two edges of said polymeric film, and a base joining said legs secured along and extending beyond a third edge of said polymeric film.

5. The medical adhesive device of claim 4, in which said U-shaped handle includes a handling tab projecting from said base thereof, away from said polymeric film.

6. A medical adhesive device comprising:
   a polymeric film;
   an adhesive coated surface comprising a first adhesive coated on a first side of said polymeric film;

a release liner covering the adhesive coated surface of said polymeric film and extending beyond at least a first edge of said polymeric film;

a handle adhered to a second non-adhesive side of the polymeric film with a pressure sensitive adhesive, with a portion of said handle projecting beyond said first edge of said polymeric film and overlying said release liner;

said first adhesive on said first side of said polymeric film adhering more aggressively to skin than said pressure sensitive adhesive adheres to said polymeric film, whereby said handle can be removed from said polymeric film once said polymeric film is adhered to a patient's skin; and wherein the handle has an undersurface that is entirely coated with said pressure sensitive adhesive, at least a portion of said pressure sensitive adhesive contacts said release liner.

7. The medical adhesive device of claim 6, wherein the pressure sensitive adhesive does not adhere to the liner and does not adhere to skin.

8. A medical adhesive device comprising at least one handle, a layer of thin, polymeric film for adhesion to a patient's skin, and a layer of release liner which underlies and extends beyond at least one edge of said polymeric film;

said layer of polymeric film having an undersurface which is coated with a layer of pressure sensitive adhesive which adheres firmly to a patient's skin, and adheres releasably to the surface of said release liner;

said handle including an undersurface which is entirely coated with a pressure sensitive adhesive which adheres firmly to the top surface of said polymeric film, but which does not adhere to said release liner or to the human skin;

said handle being secured to the top surface of said polymeric film with a portion of said handle projecting beyond the edge of said polymeric film, out over said release liner, whereby said layer of polymeric film can be removed from said release liner by grasping said extending portion of said handle and peeling said film away from said release liner, and whereby said handle can then be used to handle said polymeric film as it is applied to a patient's skin;

said adhesive on said undersurface of said polymeric film adhering more aggressively with respect to a patient's skin than said adhesive on the undersurface of said handle adheres to said polymeric film, whereby said handle can be removed from said polymeric film once said polymeric film is adhered to a patient's skin.

9. The medical adhesive device of claim 8, in which said polymeric film comprises a polyurethane film.

10. The medical adhesive device of claim 9, in which said release liner is a silicone coated release liner.

11. The medical adhesive device of claim 10, in which said adhesive coating said undersurface of said handle is acrylate-based.

12. The medical adhesive device of claim 11, in which said adhesive coating said undersurface of said polymeric film is acrylate-based.

13. The medical adhesive device of claim 12, in which said handle is generally U-shaped, having a pair of spaced legs secured along two edges of said polymeric film layer, and a base joining said legs secured along and extending beyond a third edge of said polymeric film layer.

14. The medical adhesive device of claim 13, in which said U-shaped handle includes a handling tab projecting from said base thereof, away from said polymeric film.

15. The medical adhesive device of claim 8, in which said handle is generally U-shaped, having a pair of spaced legs secured along two edges of said polymeric film layer, and a base joining said legs secured along and extending beyond a third edge of said polymeric film layer.

16. The medical adhesive device of claim 15, in which said U-shaped handle includes a handling tab projecting from said base thereof, away from said polymeric film.

17. A medical adhesive device comprising a release liner and a layer of thin polymeric film having an adhesive coated lower surface adhered to said release liner and an upper surface having a handle attached thereto to facilitate handling thereof, said handle including spaced legs adhered to said polymeric film along opposite edge portions thereof, said handle including a base portion joining said legs and being adhered along an intermediate edge portion of said polymeric film, and wherein overlapping portions of said handle and said release liner projecting beyond an edge of said polymeric film and overlap one another, and including adhesive contacting the overlapping portions.

18. A medical adhesive device comprising:
a polymeric film;
an adhesive coated surface comprising a first adhesive coated on a first side of said polymeric film;
a release liner covering the adhesive coated surface of said polymeric film and extending beyond at least a first edge of said polymeric film;
a handle adhered to a second non-adhesive side of the polymeric film with a pressure sensitive adhesive, with a portion of said handle projecting beyond said first edge of said polymeric film and overlying said release liner, wherein the handle has an undersurface that is entirely coated with the pressure sensitive adhesive and the pressure sensitive adhesive does not adhere to the liner and does not adhere to a patient's skin;
said first adhesive on said first side of said polymeric film adhering more aggressively to skin than said pressure sensitive adhesive adheres to said polymeric film, whereby said handle can be removed from said polymeric film once said polymeric film is adhered to a patient's skin.

19. A medical adhesive device comprising:
a polymeric film having a first side, a second side and a first edge;
a first adhesive coating substantially the entire first side of said polymeric film;
a release liner covering the first side of said polymeric film and having a portion extending beyond at least the first edge of said polymeric film;
a handle having a lower side that is substantially entirely coated with a pressure sensitive adhesive, the pressure sensitive adhesive adhering the handle to the second side of the polymeric film, with a portion of said handle projecting beyond said first edge of said polymeric film and overlying a portion of said release liner, wherein the portion of the handle projecting beyond the first edge of said film defines a handle edge, and wherein a portion of the release liner projects beyond the handle edge;
said first adhesive on said first side of said polymeric film adhering more aggressively to skin than said pressure sensitive adhesive adheres to said polymeric film, whereby said handle can be removed from said polymeric film once said polymeric film is adhered to a patient's skin.

20. The medical adhesive device of claim 19, wherein:
the handle has an enlarged central opening.

21. The medical adhesive device of claim 19, wherein:
the handle comprises a single layer of material.

22. The medical adhesive device of claim 19, wherein:
the handle has a generally quadrilateral perimeter.

23. A medical adhesive device comprising:

a polymeric film;

an adhesive coated surface comprising a first adhesive coated on a first side of said polymeric film;

a release liner covering the adhesive coated surface of said polymeric film and extending beyond at least a first edge of said polymeric film;

a handle having a lower side, said handle adhered to a second non-adhesive side of the polymeric film with a pressure sensitive adhesive that covers substantially the entire lower side of the handle, with a portion of said handle projecting beyond said first edge of said polymeric film and overlying said release liner, wherein substantially all of the pressure sensitive adhesive on the portion of the handle projecting beyond said first edge of said polymeric film is exposed to said release liner and unobstructed by a separate release liner;

said first adhesive on said first side of said polymeric film adhering more aggressively to skin than said pressure sensitive adhesive adheres to said polymeric film, whereby said handle can be removed from said polymeric film once said polymeric film is adhered to a patient's skin.

24. The medical adhesive device of claim 23, wherein:
the handle has an enlarged central opening.

25. The medical adhesive device of claim 23, wherein:
the handle comprises a single layer of material.

26. The medical adhesive device of claim 23, wherein:
the handle has a generally quadrilateral perimeter.

27. A medical adhesive device comprising:

a continuous polymeric film that is void of weakened areas, and having substantially uniform strength;

an adhesive coated surface comprising a first adhesive coated on a first side of said polymeric film;

a release liner covering the adhesive coated surface of said polymeric film and extending beyond at least a first edge of said polymeric film;

a handle adhered to a second non-adhesive side of the polymeric film with a pressure sensitive adhesive, with a portion of said handle projecting beyond said first edge of said polymeric film and overlying said release liner;

said first adhesive on said first side of said polymeric film adhering more aggressively to skin than said pressure sensitive adhesive adheres to said polymeric film, whereby said handle can be removed from said polymeric film once said polymeric film is adhered to a patient's skin.

28. The medical adhesive device of claim 27, wherein:
the handle has an enlarged central opening.

29. The medical adhesive device of claim 27, wherein:
the handle comprises a single layer of material.

30. The medical adhesive device of claim 27, wherein:
the handle has a generally quadrilateral perimeter.

31. A medical adhesive device comprising:

a one-piece polymeric film layer;

an adhesive coated surface comprising a first adhesive coated on a first side of said polymeric film;

a one-piece release liner layer covering the adhesive coated surface of said polymeric film layer and extending beyond at least a first edge of said polymeric film layer;

a one-piece handle layer adhered to a second non-adhesive side of the polymeric film with a pressure sensitive adhesive, with a portion of said handle projecting beyond said first edge of said polymeric film and overlying said release liner, said handle having an enlarged central opening;

said first adhesive on said first side of said polymeric film adhering more aggressively to skin than said pressure sensitive adhesive adheres to said polymeric film, whereby said handle can be removed from said polymeric film once said polymeric film is adhered to a patient's skin, and wherein:

the polymeric film layer, the release liner, and the handle layer comprise the sole non-adhesive components of said medical adhesive device.

32. The medical adhesive device of claim 31, wherein:
the handle has an enlarged central opening.

33. The medical adhesive device of claim 31, wherein:
the handle comprises a single layer of material.

34. The medical adhesive device of claim 31, wherein:
the handle has a generally quadrilateral perimeter.

* * * * *